United States Patent [19]

Wonder et al.

[11] Patent Number: 5,234,413

[45] Date of Patent: Aug. 10, 1993

[54] INFUSION RATE REGULATOR DEVICE

[76] Inventors: Terry M. Wonder, 3402 S. 3610 East, Salt Lake City, Utah 84109; Valdon G. Reynolds, 3869 S. 850 West, Bountiful, Utah 84010; Donald D. Brose, 3767 Hillside La., Holladay, Utah 84109

[21] Appl. No.: 814,072

[22] Filed: Dec. 24, 1991

Related U.S. Application Data

[63] Continuation of Ser. No. 385,554, Jul. 25, 1989, abandoned.

[51] Int. Cl.⁵ ............................................. A61M 5/00
[52] U.S. Cl. ...................................... 604/248; 604/246
[58] Field of Search .................... 604/246, 248, 251; 251/208

[56] References Cited

U.S. PATENT DOCUMENTS

| | | | |
|---|---|---|---|
| 1,964,300 | 6/1934 | Perry et al. | 158/115 |
| 2,236,084 | 3/1941 | Brown | 138/43 |
| 2,506,179 | 5/1950 | Taplin | 138/43 |
| 2,771,878 | 11/1956 | Folland et al. | 128/214 |
| 2,911,008 | 11/1959 | Du Bois | 137/625.31 |
| 3,233,457 | 2/1966 | Martinez | 73/198 |
| 3,298,367 | 1/1967 | Bergman | 128/214 |
| 3,323,774 | 6/1967 | Wilson | 604/251 X |
| 3,532,126 | 10/1070 | Boothe | 138/43 |
| 3,630,484 | 12/1971 | Taylor | 251/208 |
| 3,877,428 | 4/1975 | Seagle et al. | 128/214 R |
| 4,738,665 | 4/1988 | Shepard | 604/248 |
| 4,802,506 | 2/1989 | Aslanian | 604/248 X |

Primary Examiner—Robert P. Swiatek
Assistant Examiner—L. Thomas
Attorney, Agent, or Firm—Berne S. Broadbent

[57] ABSTRACT

A novel fluid flow regulating device for varying the rate of flow of fluids for infusion to a patient at extremely low but constant flow rates. The regulator device is interposed at a point on a supply tube between a fluid reservoir and a patient. An input port directs fluid to a fluid metering groove of variable cross-sectional area on a metering plate which is formed as a part of the output port. The metering plate is rotated axially, relative to the input port, allowing fluid to enter the fluid metering groove at any point and flow toward the output port through a fluid metering groove which increases in depth or cross-sectional area at an essentially constant rate. Depending on the point at which the fluid enters the fluid metering groove flow path, the flow rate selected can be any rate from full off to full flow.

13 Claims, 2 Drawing Sheets

INFUSION RATE REGULATOR DEVICE

This application is a continuation of our co-pending application Ser. No. 07,385,554, filed on Jul. 25, 1989 for INFUSION RATE REGULATOR DEVICE, now abandoned.

BACKGROUND

The Field of the Invention

This invention relates to an improved fluid flow regulator apparatus. More particularly, this invention relates to a novel device for regulating fluid flow to a patient in applications requiring consistent, low, but adjustable flow rates.

The Background Art

Heretofore, parenteral fluids have been administered through systems comprising a fluid reservoir and a cannula or catheter attached to each other by a flexible, elongated delivery tube. Typically, the fluid reservoir was placed above the patient, the catheter was inserted into a blood vessel of the patient and the fluid in the reservoir flowed by gravity feed through the delivery tube and into the patient. The fluid to be delivered could contain blood constituents, medication, nutritional substances and the like.

Under one system, the rate of infusion of fluid into the patient was regulated by selectively collapsing one segment of the delivery tube to restrict the flow of fluid. After the tube was collapsed, the resulting restriction on the rate of flow could be observed through a clear drip chamber interposed at a point on the delivery tube near the fluid reservoir. While this means is generally adequate in situations involving comparatively high rates of fluid flow and where accuracy is not of critical importance, it is not well suited to the control of lower fluid flow rates when greater accuracy is typically required.

In circumstances in which flow rate is of critical importance, another system of regulating the rate of parenteral infusion that has heretofore been utilized is disclosed in U.S. Pat. No. 3,877,428. This device provides a capillary flow path of variable length which regulates fluid flow, ostensibly at an essentially uniform rate, between full flow and zero flow. The device, however, is manufactured with five parts comprising a fluid receiving port, a first rubber washer, a central metering plate, a second rubber washer, and a fluid delivery port.

Use of such a large number of parts in this context has resulted in several disadvantages. First, the cost of parts and labor to manufacture the device is quite high. Second, the process of assembling and connecting the parts frequently results in an unacceptably high degree of variance in the tightness of fit between the metering plate and the two washers, thus adversely impacting the consistency of flow rate at any one meter setting. Third, possible variations in flow rate due to assembly are further exaggerated by the use of five separate parts which each have potential variations in size.

BRIEF SUMMARY AND OBJECTS OF THE INVENTION

In view of the foregoing, it is a primary object of the present invention to provide a novel, continuously variable flow regulator device for infusion of fluids with improved consistency of flow rate.

It is also an object of the present invention to reduce the cost of manufacturing infusion rate control devices by reducing the number of parts and improving the design and method of assembly.

Consistent with the foregoing objects, and in accordance with the invention as embodied and broadly described herein, a novel infusion rate regulator device is disclosed in one embodiment of the present invention as including a first member with at least one substantially smooth surface, said first member having a fluid metering groove formed in said substantially smooth surface. The fluid metering groove terminates at one end in a first fluid port which communicates with the fluid metering groove, and the fluid metering groove has a cross-sectional area which decreases substantially continuously as the distance along the groove and away from the first fluid port increases. The device also includes a second member having a second fluid port. The second member is slidably positioned adjacent the first member such that the second fluid port can be selectively positioned over a portion of the fluid metering groove so as to be in substantially direct communication with said portion of the fluid metering groove. Finally, means (such as, for example, a resilient gasket), is provided for forming a substantially fluid-tight seal over the remaining portions of the fluid metering groove, whereby fluid flowing into one fluid port is substantially confined within the fluid metering groove and conveyed to the other fluid port.

As set out further below, this invention provides, with improved consistency and reduced cost, continuously variable regulation of the rate of flow of fluids for infusion. This invention is particularly well suited to use in connection with parenteral infusion when low fluid flow rates are desired. This invention may also advantageously be used in other applications requiring the infusion of fluids, such as, for example, hyperalimentation.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENT

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 5, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

Figure 1:
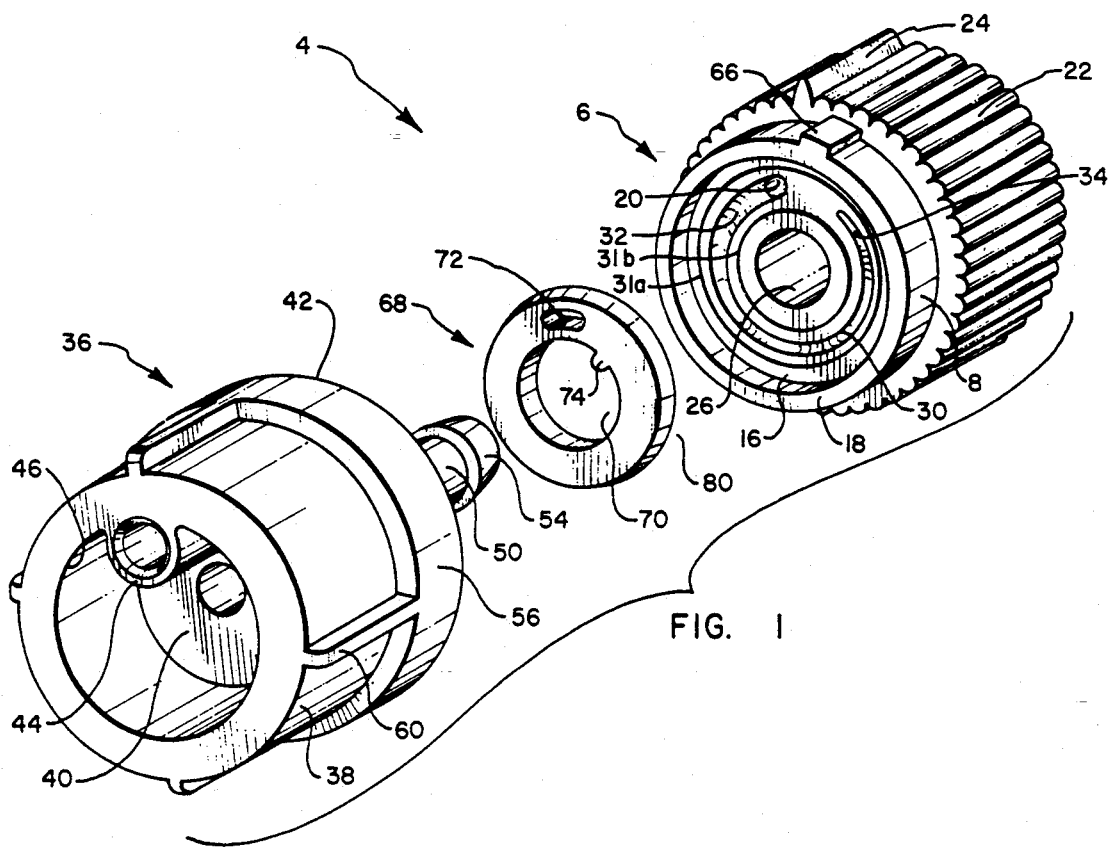
FIG. 1 is an exploded perspective view illustrating one presently preferred embodiment of the infusion rate regulator device of the present invention.
Figure 2:
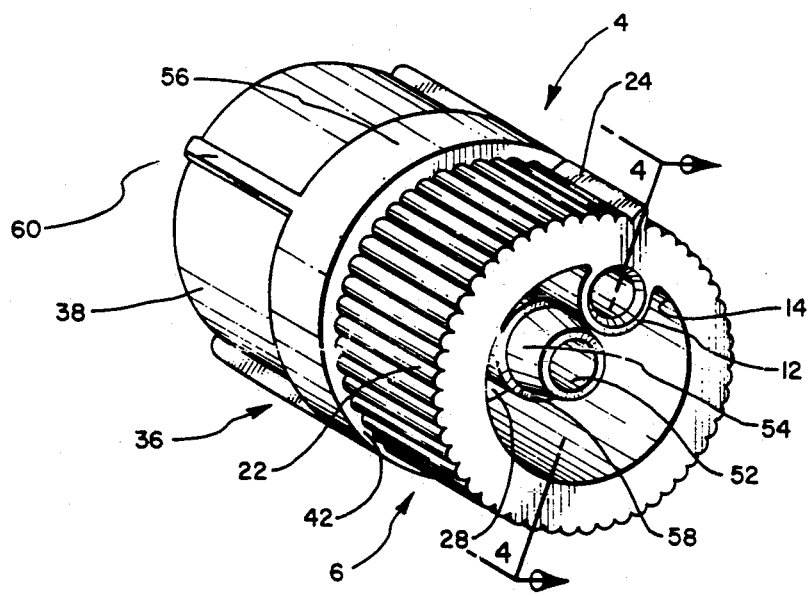
FIG. 2 is a perspective view showing the embodiment of FIG. 1 following assembly.

Referring particularly to FIG. 1, the fluid flow regulator device, generally designated 4, is illustrated. The regulator device has a fluid delivery member 6 including a cylindrical body 8 which projects inwardly a female coupling 12, more clearly visible in FIG. 2. The female coupling 12 is sized to mate in fluid-tight relationship with conventional fluid delivery tubing and is preferably tapered as shown in FIG. 2 to facilitate the insertion of such tubing. The female coupling 12 is eccentrically located adjacent the inside periphery 14 of the cylindrical body 8.

The cylindrical body 8 circumscribes and is formed integrally with a metering plate 16 which is recessed away from the leading edge 18 of the cylindrical body 8. As shown, the metering plate 16 provides a substantially smooth surface, which, as used herein, means that the surface is substantially free from roughness and projections. The metering plate 16 is provided with a through-bore 20 which is disposed in alignment with the female coupling 12 and is in open fluid communication, therewith. The metering plate 16 is shown in cross-sectional detail in FIG. 4.

Figure 4:
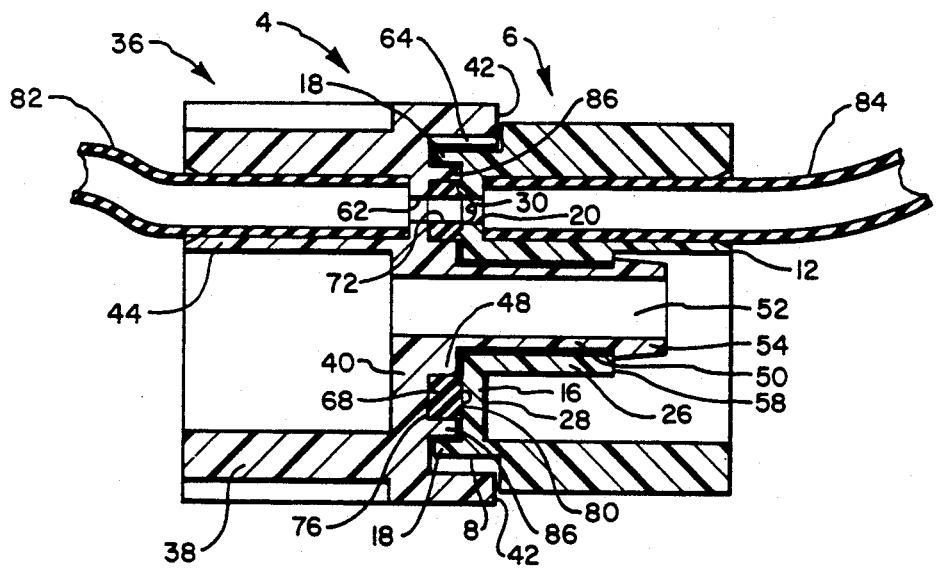
FIG. 4 is a vertical cross-sectional view of the embodiment of FIGS. 1 and 2, taken along lines 4—4 of FIG. 2.

Raised elements 22 may be formed on the exterior periphery of the cylindrical body 8 to facilitate controlled gripping of the delivery member 6. Also, if desired, at least one of the raised elements 24 may be marked or otherwise differentiated from the other raised elements 22 to identify the location of the through-bore 20. As shown, the raised elements 22 preferably do not extend onto that portion of the cylindrical body 8 which fits under the trailing edge 42 of the cylindrical body 38 of the receiving member 36 when the regulator device 4 is assembled, as depicted in FIGS. 2 and 4.

A female coupling 26 is formed integrally with and is centered with respect to the metering plate 16. The female coupling 26 is concentric with the cylindrical body 8 and extends axially from the back side 28 of the metering plate 16 as depicted in FIG. 2.

The metering plate 16 presents an open fluid metering groove 30 which is illustrated herein as being concentric with the metering plate 16 and as being in the configuration of an open, incomplete circle. The term fluid metering groove, as used herein, means an elongated passageway which affects the flow rate of fluid along its length in accordance with the varying cross-sectional area of the fluid metering groove. As used herein, the term cross-sectional area means the area defined by the groove on a plane which passes through the groove so as to be substantially perpendicular to the direction of fluid flow in the groove.

The fluid metering groove 30 is illustrated herein as an open groove which is substantially semi-circular in cross-sectional shape. It will be readily appreciated, however, that other cross-sectional shapes are possible. For example, in one presently preferred embodiment, groove 30 is substantially rectangular in cross-section and substantially the same width along its entire length, the variation in the cross-sectional area of the groove being provided by varying the depth of groove 30 along its length.

The end of the fluid metering groove 30 adjoining and in fluid communication with the through-bore 20 has approximately the same or smaller cross-sectional area as that of the through-bore 20. The cross-sectional area of the fluid metering groove 30 decreases at an approximately constant rate as the distance from the through-bore 20 end 32 of the fluid metering groove 30 increases, until the opposite end 34 of the fluid metering groove 30 effectively terminates for lack of cross-sectional area.

Figure 3:
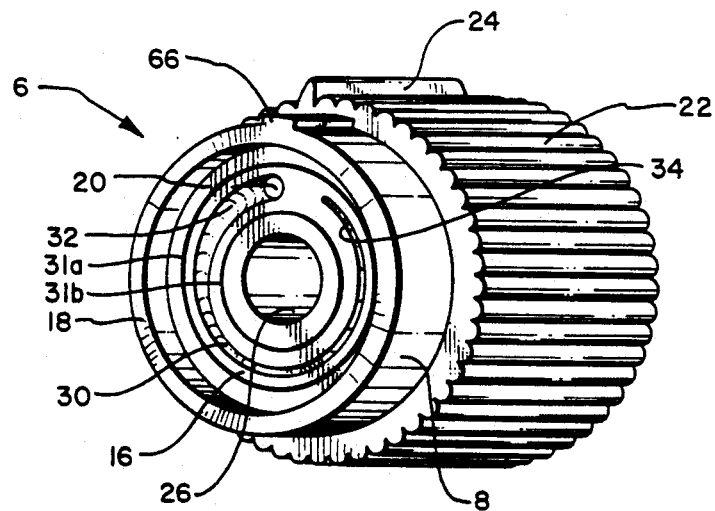
FIG. 3 is a perspective illustration of one presently preferred embodiment of the fluid delivery member and associated fluid metering groove of the device of the present invention.

Substantially circular sealing ridges 31a and 31b are preferably provided on either side of fluid metering groove 30, as illustrated in FIGS. 1 and 3. Sealing ridges 31a and 31b assist in forming a fluid-tight seal over fluid metering groove 30, as described in further detail below.

In continuing reference to FIG. 1, the fluid flow regulator 4 has a fluid receiving member designated 36 which is generally cylindrical in configuration. The receiving member 36 has an elongated cylindrical body 38 which is preferably long enough in axial dimension to allow the body 38 to be grasped easily with the fingers. The cylindrical body 38 of the receiving member 36 circumscribes a first annular disc 40, more clearly visible in FIG. 5, which is recessed away from the trailing edge 42 of the body 38. The receiving member 36 projects inwardly a female coupling 44. Like the female coupling 12 of the fluid delivery member 6, the female coupling 44 is sized to mate in fluid-tight relationship with conventional fluid delivery tubing, and is preferably tapered, as shown, to facilitate the insertion of the tubing. Also, the female coupling 44 is eccentrically located adjacent the inside periphery 46 of the cylindrical body 38.

Figure 5:
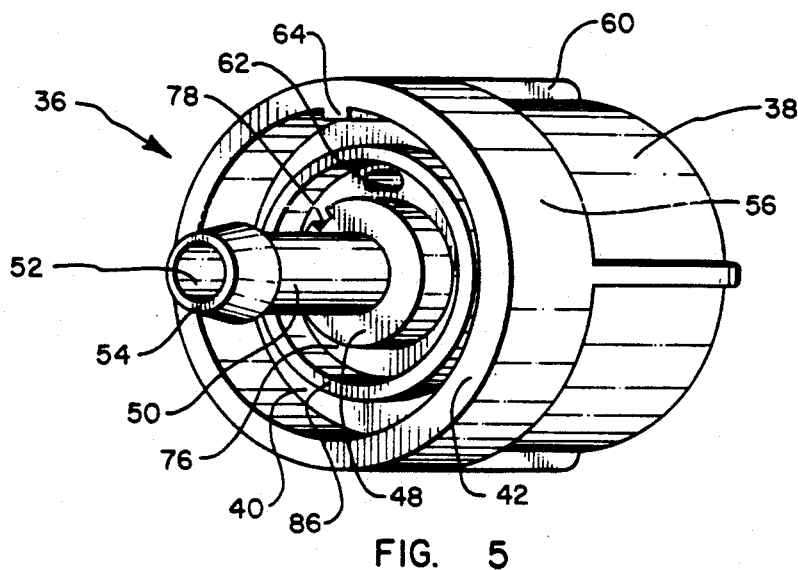
FIG. 5 is a perspective illustration of one presently preferred embodiment of the fluid receiving member of the device of the present invention.

As depicted in FIG. 5, a second annular disc 48 extends axially from, is concentric with, and is formed integrally with the first annular disc 40. The second annular disc 48 is also recessed in relation to the trailing edge 42 of the body 38. Extending axially from, concentric with, and formed integrally with the second annular disc 48 is a bearing shaft 50. The bearing shaft 50 defines a space 52 which in the preferred embodiment illustrated herein is shown as being open. This space 52 may alternatively be filled with any suitable material.

A groove 76 in the configuration of a closed circle of uniform cross-sectional area and concentric with the annular discs 40 and 48 is formed in the second annular disc 48 and is of sufficient area to accommodate snugly the annular gasket 68 described in further detail below.

An annularly enlarged, radially projecting lip 54 is integrally formed on the distal end of the bearing shaft 50 and is of sufficiently small diameter to permit the lip 54 to fit snugly through the female coupling 26 of the fluid delivery member 6, but of sufficiently large diameter and placed in such a position as to hold the delivery member 6 and receiving member 36 firmly but rotatably together in press-fit relation by snapping over the trailing edge 58 of the female coupling 26.

Significantly, the gasket 68 described below is the only sealing member inside the housing. There is no fluid-tight engagement between rigid plastic parts. When initially assembled, the gasket 68 first touches metering plate 16 (see FIG. 4) and is then compressed until the unit locks together. Ideally, there is no plastic engagement between the receiving and delivery member faces at this point. They are, however, very close to touching, and should any opposing lateral forces be applied to the opposing members, ridge 86 (see FIGS. 4 and 5) on fluid receiving member 36 will engage the outer surface of the metering plate 16 to prevent additional gasket compression on one side and lifting on the other as a result of lateral torquing. This provides a stop, but, should the parts be constantly engaged, it would generally cause too much rotational friction between the parts. Therefore, ridge 86 is preferably either almost, or just barely, touching metering plate 16 when the unit is in its unstressed state.

A silicon or other compatible lubricant may and is preferably applied to the bearing shaft 50 or between the surfaces of the disc 48 and the metering plate 16 or in both locations to facilitate low friction, wear-resistant, rotatability while maintaining fluid-tight sealing of the gasket 68 and the metering plate 16 and uniform compression of the gasket 68 into the fluid metering groove 30.

The trailing edge 42 of the cylindrical body 38 of the fluid receiving member 36 may be, and is in the illustrated preferred embodiment, integrally formed with an annularly enlarged, radially projecting flange 56. Indicia (not shown) representing flow rates or other useful information may be placed on the flange 56. Also, raised elements 60 may be formed on the exterior periphery of the cylindrical body 38 to facilitate controlled gripping of the receiving member 36.

The second annular disc 48 of the receiving member 36 is provided with a through-bore 62, as depicted in FIG. 4, which is disposed in alignment with the female coupling 44 of the receiving member 36 and is in open fluid communication therewith. While it will be appreciated that the through-bore 62 may have virtually any suitable shape, through-bore 62 is illustrated herein as being in the form of an arcuate slot, such a configuration helping to insure the proper alignment of through-bore 62 with the other components of regulator device 4.

In the preferred embodiment, a key 64 situated in alignment with the through-bore 62 of the receiving member 36 projects partially into the space between the trailing edge 42 and second annular disc 48, and extends from the trailing edge 42 to the first annular disc 40. When the delivery member 6 and the receiving member 36 are assembled and rotated, the key 64 at one point of rotation comes into contact with an inverse key 66 formed integrally on the exterior periphery of the leading edge 18 portion of cylindrical body 8. The inverse key 66 is situated such that when the key 64 comes into contact with the inverse key 66 in home position, as illustrated in exploded perspective in FIG. 1, the through-bore 20 of the delivery member 6 is aligned with the corresponding through-bore 62 in the receiving member 36. When rotated counterclockwise in the opposite direction, until the two keys 64 and 66 come into contact on opposite sides, the two through-bores 20 and 62 are out of alignment and, since through-bore 62 is also out of alignment with the metering groove 30, there is no fluid communication between the through-bores 20 and 62 through the fluid metering groove 30 or otherwise, as will become more readily apparent from the discussion which follows.

An annular gasket 68 preferably formed of an elastomeric compound is formed with an aperture 70 and circumference sized to snugly fit and displace the area of the groove 76 in the second annular disc 48. The gasket 68 has a through-bore 72 which is similar in size to the through-bore 62 of the receiving member 36, and a nodule 74 projecting into the aperture 70 from the inner periphery of the gasket 68. In current design, the nodule 74 is located approximately 25 degrees from the through-bore 72 in order to minimize the potential for compression of gasket 68 into the through-bore 72.

When the gasket 68 is snugly fit into the groove 76, the nodule 74 is to be positioned so as to fit snugly within the slot 78. The nodule 74 is positioned within the slot 78 for the purpose of ensuring that the through-bore 62 of the receiving member 36 is aligned and in fluid communication with the through-bore 72 of the gasket 68.

The transverse dimension of the gasket 68 is selected so that the exposed face 80 of the gasket 68 will fit snugly against the surface of the metering plate 16. When the regulator device 4 is assembled (FIG. 2), the exposed face 80 of the gasket 68 completely covers the fluid metering groove 30 in sealed, fluid-tight relation. Nevertheless, the gasket 68 does not fit so tightly as to displace a significant portion of the cross-sectional area of the fluid metering groove 30.

When using the invention as illustrated in FIG. 4, the regulator device 4 is situated at any preferred location along a flexible elongated intravenous delivery tube 82, 84. One portion 82 of the tube is press-fit and bonded (such as, for example, with a suitable solvent cement), in mating fashion into, and in fluid-tight relation with, the female coupling 44 of the receiving member 36 to introduce fluid into the regulator device 4. Another portion 84 of the tube is similarly press-fit and in mating fashion into, and in fluid-tight relation with, the female coupling 12 of the delivery member 6 so as to direct fluid away from the regulator device 4.

When the two keys 64 and 66 are in contact and the through-bore 20 of the delivery member 6 is aligned with the through-bores 72 and 62 of the gasket 68 and the receiving member 36, respectively, as illustrated in FIGS. 1 and 4, the invention is positioned to provide maximum fluid flow. In this position, resistance to flow through the device 4 will be generated only due to the reduced diameters of the through-bores 20, 62, and 72 with respect to the diameter of tubes 82, 84.

As the delivery member 6 and the receiving member 36 are rotated in counterclockwise relation to each other, fluid is directed from through-bore 62 of the receiving member 36 into the fluid metering groove 30. Importantly, at the point where fluid enters the metering groove 30, the cross-sectional area of the groove 30 is less than that of the through-bore 20. As fluid then flows along the groove 30 toward the through-bore 20, the cross-sectional area of the groove 30 increases until the fluid ultimately flows into through-bore 20. Upon further counterclockwise rotation of delivery member 6 and receiving member 36, fluid passing through the receiving through-bore 62 must pass through a space in the fluid metering groove 30 of increasingly smaller cross-sectional area to effect fluid communication with the delivery through-bore 20. When the counterclockwise rotation is complete and the two keys 64 and 66 come into close proximity or contact on opposite sides, the fluid metering groove 30 will have diminished in cross-sectional area so as to have effectively terminated. In this position, fluid flow through the regulator device 4 is completely restricted.

The rate of fluid flow through the regulator device 4 is a function not only of the length of the fluid metering groove 30 through which fluid flows. Rather, the rate of fluid flow is principally a direct, exponential function of the cross-sectional area of the fluid metering groove 30 at the point which the fluid from the receiving through-bore 62 is first introduced, as well as the tapered cross-sectional area of the entire flow path through the groove 30. For illustrative purposes, where fluid is introduced at a point along the fluid metering groove 34 which is of relatively small cross-sectional area, the fluid will progress toward the delivery through-bore 20 by proceeding through a portion of the fluid metering groove which is of increasingly large cross-sectional area. Accordingly, infusion control devices with complicated, multiple capillaries are no longer necessary to obtain accurate regulation of extremely low flow rates, making the regulator device 4 highly advantageous over the prior art. Accuracy of flow rates will be improved if the pressure differential across device 4 is substantially constant.

Variations from the specific embodiment described above are, of course possible. It is observed that the female couplings 12 and 44 could be alternatively configured as male couplings. Also, it will be readily appreciated that members 6 and 36 could be slidably coupled to one another in non-rotating fashion (such as, for example, linearly), and still maintain the necessary functional relationship between the component parts.

The components can, of course, be formed of a wide variety of suitable materials. Members 6 and 36 may, for example, be formed of a plastic material, preferably one which is dimensionally stable when exposed to liquids and when exposed to temperatures below approximately 150 degrees Fahrenheit. The gasket may, for example, be formed of silicone, rubber, or any other suitable resilient material.

From the above discussion, it will be appreciated that the present invention provides a continuously variable flow regulator device for infusion of fluids with improved consistency of flow rate. Moreover, since the device of the present invention has only three, easily assembled parts, the present invention also serves to reduce the cost of manufacturing and assembling infusion rate control devices.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A device for regulating the flow of fluid to a patient through a fluid delivery tube, the device comprising:
   a first member with at least one substantially smooth surface, said first member having a fluid metering groove formed in said substantially smooth surface, the fluid metering groove terminating at one end in a first fluid port which communicates with the fluid metering groove, and the fluid metering groove having a cross-sectional area which decreases substantially continuously as the distance along the groove and away from the first fluid port increases;
   means associated with said first member for retaining a portion of said fluid delivery tube in communication with said first fluid port;
   a second member having a second fluid port, the second member being slidably positioned adjacent the first member such that the second fluid port can be selectively positioned over a portion of the fluid metering groove so as to be in substantially direct communication with said portion of the fluid metering groove;
   means associated with said second member for retaining a portion of said fluid delivery tube in communication with said second fluid port; and
   means for forming a substantially fluid-tight seal over all portions of the fluid metering groove other than said portion which is in substantially direct communication with said second fluid port, such that substantially all fluid flowing from said fluid delivery tube into one fluid port is confined within and conveyed through the fluid metering groove to the other fluid port.

2. A device for regulating the flow of fluid to a patient as defined in claim 1 wherein the substantially smooth surface of the first member is substantially planar.

3. A device for regulating the flow of fluid to a patient as defined in claim 2 wherein the first and second members are rotatable with respect to one another about an axis, wherein the substantially smooth, planar surface of the first member is substantially perpendicular to said axis, and wherein fluid metering groove lies in a substantially circular, concentric ring about said axis.

4. A device for regulating the flow of fluid to a patient as defined in claim 1 wherein the first and second members are substantially cylindrical in shape.

5. A device for regulating the flow of fluid to a patient as defined in claim 1 wherein the fluid metering groove of the first member decreases substantially continuously to near zero as the distance along the groove and away from the first fluid port increases.

6. A device for regulating the flow of fluid to a patient as defined in claim 1 wherein the means for forming a substantially fluid-tight seal comprises a resilient gasket.

7. A device for regulating the flow of fluid to a patient as defined in claim 6 wherein said gasket is positioned between said first and second members.

8. A device for regulating the flow of fluid to a patient as defined in claim 7 wherein the second member has a ridge which abuts the first member upon compression of the gasket, thereby limiting the possible compression of the gasket.

9. A device for regulating the flow of fluid to a patient as defined in claim 6 wherein said gasket has a bore therethrough and said second fluid port communicates with said portion of the fluid metering groove through said bore.

10. A device for regulating the flow of fluid to a patient through a fluid delivery tube, the device consisting essentially of:
   a first member with at least one substantially smooth surface, said first member having a fluid metering groove formed in said substantially smooth surface, the fluid metering groove terminating at one end in a first fluid port which communicates with the fluid metering groove, and the fluid metering groove having a cross-sectional area which decreases substantially continuously as the distance along the groove and away from the first fluid port increases;

means associated with said first member for retaining a portion of said fluid delivery tube in communication with said first fluid port;

a second member having a second fluid port, the second member being slidably positioned adjacent the first member such that the second fluid port can be selectively positioned over a portion of the fluid metering groove so as to be in substantially direct communication with said portion of the fluid metering groove;

means associated with said second member for retaining a portion of said fluid delivery tube in communication with said second fluid port; and means for forming a substantially fluid-tight seal over all portions of the fluid metering groove other than said portion which is in substantially direct communication with said second fluid port, such that substantially all fluid flowing from said fluid delivery tube into one fluid port is confined within and conveyed through the fluid metering groove to the other fluid port.

11. A device for regulating the flow of fluid to a patient as defined in claim 10 wherein the substantially smooth surface of the first member is substantially planar.

12. A device for regulating the flow of fluid to a patient as defined in claim 11 wherein the first and second members are rotatable with respect to one another about an axis, wherein the substantially smooth, planar surface of the first member is substantially perpendicular to said axis, and wherein fluid metering groove lies in a substantially circular, concentric ring about said axis.

13. A device for regulating the flow of fluid to a patient as defined in claim 10 wherein the means for forming a substantially fluid-tight seal comprises a resilient gasket.

* * * * *